United States Patent [19]

Fang et al.

[11] Patent Number: 5,869,527
[45] Date of Patent: Feb. 9, 1999

[54] 6-(N-CARBOXYMETHYLAMINO) CAPROATE, SALTS THEREOF AND METHODS OF USE THEREFOR

[75] Inventors: Sheng-Ding Fang, Mahwah; Michael E. Lankin, Cedar Grove; Henry W. Founds, Mendham; David H. Shih, Lawrenceville, all of N.J.

[73] Assignee: Alteon Inc., Ramsey, N.J.

[21] Appl. No.: 771,958

[22] Filed: Dec. 23, 1996

Related U.S. Application Data

[60] Provisional application No. 60/009,442 Dec. 29, 1995.
[51] Int. Cl.[6] .................................................. A61K 31/235
[52] U.S. Cl. ............................................................. 514/533
[58] Field of Search ............................................ 514/533

[56] References Cited

U.S. PATENT DOCUMENTS

| | | | |
|---|---|---|---|
| 2,562,198 | 7/1951 | McKinney et al. | 260/511 |
| 2,607,797 | 8/1952 | McKinney et al. | 260/471 |
| 4,758,583 | 7/1988 | Cerami et al. | 514/399 |
| 4,946,778 | 8/1990 | Ladner et al. | 435/69.6 |

FOREIGN PATENT DOCUMENTS

| | | |
|---|---|---|
| 0 101 588 | 2/1984 | European Pat. Off. . |
| 0101588 | 2/1984 | European Pat. Off. ..... A61K 31/195 |
| WO 90/13678 | 11/1990 | WIPO . |

OTHER PUBLICATIONS

Bucala et al., in Advances in Pharmacology, vol. 23, pp. 1–34, Academic Press (1992).
Chang et al., J. Biol. Chem., 260:7970–7974, 1985.
Cole et al., 1985, in Monoclonal Antibodies and Cancer Therapy, Alan R. Liss, Inc., pp. 77–96.
Cote et al., 1983, Proc. Natl. Acad. Sci. U.S.A. 80:2026–2030.
Dell et al. (1980) Fresenius Z. Anal. Chem. 304:407–11.
Dell et al. (1981) Chem. Abst.94:6–7 (185281z).
Engelsma et al. (1980) Chem. Abst. 92:274 (17742r).
Engelsma et al. (1979) Lebensm.–Wiss. u. –Technol. 12:203–7.
Huse et al., 1989, Science 246:1275–1281.
Kohler and Milstein (1975, Nature 256:495–497).
Kozbor et al., 1983, Immunology Today 4:72.
Kyte, J.(1972) J. Biol. Chem. 247:7634–41.
Kyte, J.(1973) Chem. Abst. 78:232 (54806w).
Morrison et al., 1984, J. Bacteriol. 159–870.
Neuberger et al., 1984, Nature 312:604–608.
Rowley et al. (1971) J. Am. Chem. Soc. 93:5542–51.
Takeda et al., 1985, Natue 314:452–454.

*Primary Examiner*—Russell Travers
*Attorney, Agent, or Firm*—Klauber & Jackson

[57] ABSTRACT

Compounds useful in the production and analysis of monoclonal antibodies to advanced glycosylation endproducts are 6-(N-carboxymethylamino)caproates of the formula $$XO_2C—(CH_2)_5—NH—CH_2CO_2X \qquad (I)$$

wherein X is hydrogen or an alkali metal salt cation. These compounds can be used in the production of such monoclonal antibodies, and to assess the purity and reactivity of AGE-antibodies produced for diagnostic purposes.

4 Claims, No Drawings

6-(N-CARBOXYMETHYLAMINO) CAPROATE, SALTS THEREOF AND METHODS OF USE THEREFOR

This application claims priority from U.S. provisional application Ser. No. 60/009,442, filed Dec. 29, 1995.

BACKGROUND OF THE INVENTION

The present invention relates a synthetic compound which serves as an antigen for recognition by a monoclonal antibody to advanced glycosylation endproducts.

It has been discovered that the protein glycosylation and the resultant formation of crosslinks leads to what has become known as advanced glycosylation (glycation) endproducts and cross-links. The nonenzymatic reaction between glucose and the free amino groups on proteins to form a stable, 1-deoxyketosyl adduct, known as the Amadori product, has been shown to occur with hemoglobin, wherein a rearrangement of the amino terminal of the beta-chain of hemoglobin by reaction with glucose, forms the adduct known as hemoglobin $A_{1c}$. The reaction has also been found to occur with a variety of other body proteins, such as lens crystallins, collagen and nerve proteins. See Bucala et al., "Advanced Glycosylation; Chemistry, Biology, and Implications for Diabetes and Aging" in *Advances in Pharmacology*, 23, pp. 1–34, Academic Press (1992).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. Interestingly, the aging of collagen can be mimicked in vitro by the cross-linking induced by glucose; and the capture of other proteins and the formation of adducts by collagen, also noted, is theorized to occur by a cross-linking reaction, and is believed to account for the observed accumulation of albumin and antibodies in kidney basement membrane.

In U.S. Pat. No. 4,758,583, a method and associated agents were disclosed that served to inhibit the formation of advanced glycosylation endproducts by reacting with an early glycosylation product that results from the original reaction between the target protein and glucose. Accordingly, inhibition was postulated to take place as the reaction between the inhibitor and the early glycosylation product appeared to interrupt the subsequent reaction of the glycosylated protein with additional protein material to form the cross-linked late-stage product. One of the agents identified as an inhibitor was aminoguanidine, and the results of further testing have borne out its efficacy in this regard.

To fully elucidate the mechanism of the formation of advanced glycosylation endproducts, and as a means of monitoring the onset and progress of diseases which occur as a result thereof, both polyclonal and monoclonal antibodies have been developed. In the course of developing these antibodies, it has been necessary to identify and characterize antigens which are recognized thereby. During the isolation and development of the antibodies of co-pending U.S. Ser. No. 08/367,507, filed Dec. 28, 1994, the antigen of the present invention was isolated and characterized.

SUMMARY OF THE INVENTION

In accordance with the present invention, there are disclosed compounds useful in the production and analysis of monoclonal antibodies to advanced glycosylation endproducts. These compounds are 6-(N-carboxymethylamino) caproates of the formula

$$XO_2C-(CH_2)_5-NH-CH_2CO_2X \qquad (I)$$

wherein X is hydrogen or an alkali metal salt cation.

These compounds can be used to produce monoclonal antibodies, and to test for the purity of such antibodies produced for diagnostic purposes.

Accordingly, it is a principal object of the present invention to provide a method for raising monoclonal antibodies to advanced glycosylation endproducts.

It is a further object of the present invention to provide a method for characterizing the purity and specificity of monoclonal antibodies to such advanced glycosylation endproducts.

It is a further object of the present invention to provide a compositions which are useful in the production of monoclonal antibodies to advanced glycosylation endproducts.

It is a yet further object of the present invention to provide compositions useful as analytical standards for determining the purity and quality of monoclonal antibodies to advanced glycosylation endproducts.

Other objects and advantages will become apparent to those skilled in the art from a consideration of the ensuing description.

DETAILED DESCRIPTION OF THE PREFERRED EMBODIMENT

In accordance with the present invention, agents, compositions including pharmaceutical compositions containing said agents and associated methods have been developed which are believed to inhibit the formation of advanced glycosylation endproducts in a number of target proteins existing in both animals and plant material.

In particular, the invention relates to 6-(N-carboxymethylamino)caproates of the formula

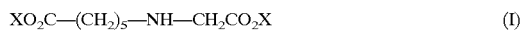

$$XO_2C-(CH_2)_5-NH-CH_2CO_2X \qquad (I)$$

wherein X is hydrogen or an alkali metal salt cation.

The alkali metal salt cations referred to above are potassium, sodium and the like, and most preferably are sodium.

For the purposes of this invention, the compounds of formula (I) can be used as the alkali metal salts (X=alkali metal) or as the free dicarboxylic amino acids (X=hydrogen).

Representative compounds of the present invention include:

disodium 6-(N-carboxymethylamino)caproate;

dipotassium 6-(N-carboxymethylamino)caproate; and 6-(N-carboxymethylamino)caproic acid.

The compounds of formula I can be prepared according to the methods described in European Published Patent Application 0 101 588, published Feb. 29, 1984. This reference describes, at page 3, the preparation of the free acid forms (X=hydrogen) of the compounds of formula I, i.e., N-methylcarboxymethylamino)caproic acid.

A preferred route of synthesis is as shown in Scheme I below.

Scheme I

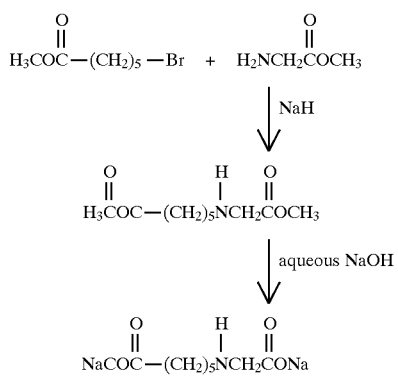

In this reaction scheme, methyl 6-bromohexanoate is alkylated with methyl glycine in the presence of sodium hydride to afford the 6-[(carboxymethyl)amino]hexanoic acid. Treatment of 6-[(carboxymethyl)amino]hexanoic acid with sodium hydroxide affords the corresponding 6-[(carboxymethyl)amino]hexanoic acid disodium salt.

The compounds of formula I are recognized by antibodies which have been determined to be capable of recognizing other advanced glycosylation endproducts, produced both in vivo and in vitro. This makes these compounds themselves capable of being used to raise monoclonal antibodies to advanced glycosylation endproducts on target proteins. They are also useful as antigens which can be used to identify monoclonal antibodies which recognize advanced glycosylation endproducts, and as standards to determine the purity of such monoclonal antibodies.

The rationale of the present invention is to use the compounds of formula I in the production of monoclonal antibodies which can then be used in various therapeutic and diagnostic methods therefor, such as those disclosed and claimed in copending U.S. Ser. No. 08/367,507, filed Dec. 30, 1994, which disclosure is specifically incorporated herein by reference, and its continuation-in-part Application, entitled "Monoclonal Antibodies Specific for Advanced Glycosylation Endproducts in Biological Samples", U.S. Ser. No. 08/581,724, filed Dec. 29, 1995, which disclosure is also specifically incorporated herein by reference.

The compounds of formula I can be used to identify monoclonal antibodies, raised either in vivo or in vitro, which recognize AGEs.

The compounds of formula I can also be used to produce antibodies to themselves using various procedures known in the art for the production of polyclonal and monoclonal antibodies. For example, reproduction of antibody may proceed by the immunization of various host animals. In this embodiment, a compound of formula I, i.e., disodium 6-(N-carboxymethylamino)caproate, may be conjugated to an immunogenic carrier, e.g., bovine serum albumin (BSA) or keyhole limpet hemocyanin (KLH), or the carrier may be reacted with a reducing sugar such as glucose such that the carrier bears AGE determinants. Various adjuvants such as those set forth above, may be used to increase the immunological response, depending on the host species.

For production of monoclonal antibodies to the compounds of formula I of the present invention, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.,* 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" or "humanized antibodies" (Morrison et al., 1984, J. Bacteriol. 159–870; Neuberger et al., 1984, *Nature,* 312:604–608; Takeda et al., 1985, *Nature,* 314:452–454) by splicing the genes from a mouse antibody molecule of the present invention, e.g., monoclonal antibody 4G9, together with genes from a human antibody molecule of appropriate biological activity can be used; such antibodies are within the scope of this invention. Chimeric antibodies are those that contain a human Fc portion and a murine (or other non-human) Fv portion; humanized antibodies are those in which the murine (or other non-human) complementarity determining regions (CDR) are incorporated in a human antibody; both chimeric and humanized antibodies are monoclonal. Such human or humanized chimeric antibodies are preferred for use in in vivo diagnosis or therapy of human diseases or disorders (described infra), since the human or humanized antibodies are much less likely than xenogeneic antibodies to induce an immune response, in particular an allergic response.

According to the present invention, techniques described for the production of single chain antibodies (U.S. Pat. No. 4,946,778) can be adapted to provide single chain antibodies of the present invention. An additional embodiment of the invention utilizes the techniques described for the construction of Fab expression libraries (Huse et al., 1989, *Science,* 246:1275–1281) to allow rapid and easy identification of monoclonal Fab fragments with the desired specificity for the antibody of the present invention, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Such antibody fragments can be generated from any of the polyclonal or monoclonal antibodies of the invention; preferably, such antibody fragments are generated using monoclonal antibody 4G9.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Many means are known in the art for detecting binding in an immunoassay and are within the scope of the present invention. For example, to select antibodies in accordance with the present invention, one may assay generated hybridomas for a product which binds to the compounds of formula I.

The foregoing antibodies can be used in methods known in the art relating to the localization and activity of AGE-modified proteins or tissues, e.g., for Western blotting, ELISA, detecting AGE-modified tissue in situ, measuring levels of AGE-modified molecules, for instance including proteins, peptides, lipids and nucleic acids, and, in particular, hemoglobin-AGE, immunoglobulin-AGE, and LDL-AGE, in appropriate physiological samples, such as serum samples.

Using an antibody to the compounds of formula I of the present invention, one can assess and/or detect the presence of stimulated, spontaneous, or idiopathic pathological states in mammals, by measuring the corresponding presence of advanced glycosylation endproducts. More particularly, since antibodies to numerous AGEs have been shown to bind to the compounds of formula I, an antibody to these compounds can be used to detect the presence or amount of AGEs by assay techniques such as those discussed herein, for example through the use of an appropriately labeled quantity of an anti-AGE monoclonal antibody, as set forth herein.

The tissue and end organ damage caused by advanced glycosylation accumulates over a period of months to years. Diabetic complications progress over a similar duration, so that it is advantageous to detect earlier the AGE accumulation that has been linked to the development of pathology in such disease states.

In particular, a monoclonal antibody to the compounds of formula I of the invention can be used to detect the presence of AGEs such as but not limited to, hemoglobin-AGE, albumin-AGE, lipid-AGEs, and AGE-modified peptides. Generally, the presence of a disease or disorder associated with AGEs can be assessed by detecting higher levels of AGEs in a biological sample from a subject who suffers from such a disease or disorder, as compared to a normal individual. The effectiveness of an agent, e.g., aminoguanidine, to prevent or inhibit the formation of AGEs can be evaluated by observing a decrease in the level of AGEs in biological samples obtained from a subject over a time interval.

For example, Hb-AGE has been determined to account for about 0.42% of circulating human hemoglobin. This fraction increases to approximately 0.75% in patients with diabetes-induced hyperglycemia. Of significance, diabetic patients treated for 28 days with aminoguanidine, an inhibitor of AGE formation in vivo, show significantly decreased levels of Hb-AGE at the end of the treatment period (International Publication No. WO 93/13421).

The present invention also extends to the measurement of other AGEs and particularly serum and urinary AGE-modified proteins and AGE-modified peptides. Serum and urinary AGE-modified peptides, like lipid-AGE and Hb-AGE, represent circulating markers of AGE accumulation that reflect the onset and extent of pathologies and other dysfunctions where such accumulation is a characteristic. Thus, those AGE-related and diabetic conditions where increased levels of AGEs have been observed, such as, for example, atherosclerosis, cataracts and diabetic nephropathy, may be monitored and assessed over the long term by the measurement of these AGEs, particularly by resort to the diagnostic methods disclosed herein.

Similarly, serum peptide-AGEs can be used as an indicator that reflects glomerular filtration rate (GFR) and kidney damage. Urinary peptide-AGEs may be used as an indicator to measure the turnover in tissue proteins, and more particularly, tissue protein bearing AGE modifications.

In the LDL-AGE, Hb-AGE, and the serum peptide-AGE assays, a blood sample is drawn and a separation procedure can be used. For measuring the level of LDL- or lipid-AGEs, a procedure such as that described in International Publication No. WO 93/13421 by Bucala et al. can be used. For detecting hemoglobin-AGE, the cellular blood components can be separated from the serum, and hemoglobin can be extracted from the red blood cells. The serum level of LDL-AGE, peptide-AGEs and the presence or extent of Hb-AGEs present can then be evaluated.

By conducting these tests with a single blood sample, a broader time frame at which blood glucose levels become uncontrolled can be estimated, e.g., a 60 day range predictable by Hb-AGE for instance, extends the period to be assessed for glycemic control to before the 3–4 week time frame which is measured by Hb-$A_{1c}$ determination. If desired, the analyses of HB-AGE and serum peptide-AGEs can be run together with a glucose level determination in blood or urine, a glucose tolerance test, and other tests useful for assessing diabetes control including the measurement of urinary peptide-AGEs, to give a complete patient profile.

In another aspect of the invention, LDL-AGEs are measured using a monoclonal antibody of the invention in combination with either an anti-LDL (such as, but not limited to, anti-ApoB) antibody or a polyclonal anti-AGE antibody (such as rabbit anti-RNase-AGE).

Another aspect of the invention addresses advanced glycosylation endproducts which can be detected in the urine. Proteins, including peptides, are excreted in the urine in very low amounts in normal individuals, and at elevated levels in diseased individuals. The presence and/or level of urinary peptide-AGEs reflective of the turnover of tissue AGEs can be determined, correlated to and predictive of particular diseases or conditions.

The presence of peptides in the urine may be a symptom of numerous diseases or conditions reflective of a net catabolic state as would exist when the host or patient is undergoing invasion as by infection. Under such circumstances, the host mobilizes against the invasive stimulus by the secretion of numerous factors such as cytokines that suspend the anabolic energy storage activity and cellular repair activities and promote instead the catabolic depletion of energy stores and the recruitment of leukocytes and other factors to fight and neutralize the stimulus. The measurement of urinary peptide-AGEs provides yet another index of possible invasive activity in the host, such as cachexia and shock. Thus, one can measure the presence or level of peptide-AGEs in urine, and correlate this level to a standard. In normal individuals, the normal level may be low. In diabetic patients, the level of peptide-AGEs may be greater. Alternatively, in a subject suffering from AGE-associated advanced renal disease, the level of urinary peptides may be greatly decreased owing to the onset of renal failure. In patients experiencing infection or other trauma, the level of peptide-AGEs may be significantly greater than in normal individuals. Thus, the advancement or worsening of diabetes prior to the onset of renal complications, the onset of renal complications associated with diabetes or other AGE-related diseases, or the presence of infection could be detected by detecting urine levels of peptide-AGEs.

A monoclonal antibody to the compounds of formula I of the invention can also be used in the treatment of patients to reduce the level or accelerate the removal of circulating AGEs or AGE-modified molecules, or similar such AGEs or AGE-modified molecules, which may be present in abnormally elevated levels in certain tissues, e.g., pancreas, liver, kidney or brain, and which AGEs may be undesired.

In accordance with standard practices, the antibody or antibodies to the compounds of the present invention can, optionally be labeled. The labels most commonly employed are radioactive element, enzymes, chemicals which fluoresce when exposed to ultraviolet light, and others A number of fluorescent material are known, and can be utilized as labels. These include, for example, fluorescein, rhodamine and auramine.

The present invention also includes assay and test kits for the qualitative and/or quantitative analysis of the extent of the presence of advanced glycosylation endproducts. Such assay systems and test kits may comprise a labeled component prepared, e.g., by one of the radioactive and/or enzymatic techniques discussed herein, coupling a label to a monoclonal antibody to the compounds of the present invention or an antigen-binding fragment thereof, or to a binding partner thereof. One of the components of the kits described herein is an monoclonal antibody of the present invention or the antigen-binding fragment thereof, in labeled or non-labeled form.

As stated earlier, the kits may be used to measure the presence of advanced glycosylation endproducts on recombinant or other purified proteins, and particularly those destined for therapeutic use, to assay them for AGE presence in a first instance, and in a second instance, to assist in their further purification free from material with undesired AGE modifications. The kits may also be used to assess the purity of other monoclonal anti-AGE antibodies.

In accordance with the testing techniques discussed above, one class of such kits will contain at least a monoclonal antibody or an antigen-binding fragment thereof of the invention, means for detecting immunospecific binding of said antibody or fragment thereof to AGE components in a biological sample, and directions, of course, depending upon the method selected, e.g., "competitive", "sandwich", "DASP" and the like. The kits may also contain peripheral reagents such as buffers, stabilizers, etc.

More specifically, the preferred diagnostic test kit may further comprise a known amount of a binding partner to an antibody as described above, generally bound to a solid phase to form an immunosorbent, or in the alternative, bound to a suitable label.

The compositions useful in the present invention comprise the 6-(N-carboxymethylamino)caproates of formula I. Such compositions can be utilized in both diagnostic and therapeutic applications.

In the instance where the compositions of the present invention are utilized for in vivo or therapeutic purposes, it may be noted that the compounds of formula I are biocompatible. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration.

A liquid form would be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the agent in a suitable vehicle such as water, ethanol, propylene glycol, perhaps including a carrier to aid in penetration into the skin or eye. For example, a topical preparation could include up to about 10% of the compound of Formula I. Other suitable forms for administration to other body tissues are also contemplated.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 30 mg/kg.

The compound of Formula I can be formulated in compositions in an amount effective to raise antibodies to advanced glycosylation endproducts. This amount will, of course, vary with the particular agent being utilized and the particular dosage form, but typically is in the range of 0.01% to 1.0%, by weight, of the particular formulation. Coupling with a suitable adjuvant prior to formulation is optional, but preferable.

The following examples are illustrative of the invention.

EXAMPLE 1

BINDING AND IMMUNOLOGICAL CHARACTERISTICS OF THE AGE-SPECIFIC MONOCLONAL ANTIBODIES

The ability of monoclonal antibodies, mAb 4G9, mAb BH4 and mAb 2G6, raised against KLH non-enzymatically glycated by prolonged incubation with glucose (KLH-AGE), to recognize the disodium 6-(N-carboxymethylamino)caproate was determined.

Materials and Methods: Production of disodium 6-(N-carboxymethylamino)caproate was by the methods described hereinabove. 6-(N-Carboxymethylamino) caproic acid disodium salt was obtained as amorphous powder. mp. 168°–170° C. $^1$H NMR (DMSO-d$_6$+D$_2$O, 400 MHz), δ 3.23 (2H, s, H-2'), 2.80 (2H, t, J=7.6 Hz, H-6), 2.08 (2H, t, J=7.3 Hz, H-2), 1.53 (2H, m, H-5), 1.44 (2H, m, H-3), and 1.23 (2H, m, H-4). $^{13}$C NMR (DMSO-d$_6$+D$_2$O, 100.53 MHz), δ 177.17(C-1), 168.81 (C-1'), 49.62 (C-6), 47.10 (C-2'), 35.50 (C-2), 25.97 (C-4), 25.53 (C-3), and 24.89 (C-5). These data based on 2D COSY and CH correlation.

Direct ELISA and competition ELISA. For direct ELISA, 6- (N-carboxymethylamino)caproate was coated on microtiter plates, the unbound sites were blocked by incubation with Assay Buffer (25 mM borate, pH 8.0, 150 mM NaCl, 0.01% EDTA and 1% BSA). The plate was washed six times and increasing concentrations of mAb in Assay Buffer were added. After this incubation, the plate was again washed and incubated with alkaline-phosphatase labeled goat anti-mouse antibodies (Cappel, Durham, N.C.) diluted 1:1000 in Assay Buffer. The unbound antibodies were removed by extensive washing and the bound antibodies were detected by addition of p-nitrophenylphosphate in recording the optical density at 410 nm.

The competition ELISA was performed by pre-coating microtiter plates with disodium 6-(N-carboxymethylamino) caproate and blocking with Assay Buffer. The plate was washed and the various monoclonal antibodies and increasing concentrations of the disodium 6-(N-carboxymethylamino)caproate was added and simultaneously incubated for 1 hour at 37° C. The unbound materials were removed by extensive washing and the bound mAb was detected with alkaline phosphatase labeled anti-mouse antibodies similar to direct ELISA. All washes were in TBS-T wash solution; all incubations proceeded for 1 hour at 37° C.

Results: Interaction of the monoclonal antibodies with disodium 6-(N-carboxymethylamino)caproate. Monoclonal antibody 4G9, American Type Culture Collection Accession Number CRL 11626 (described in Example 1 of U.S. Ser. No. 08/367,507, filed Dec. 30, 1994, the disclosure of which is incorporated by reference) and monoclonal antibodies 2G6, deposited with the American Type Culture Collection on Dec. 19, 1995 under Accession Number HB 12008, and monoclonal antibody BH4, deposited with the American Type Culture Collection on Dec. 29, 1995 under Accession Number ZZZ, (both described in Example 10 of U.S. Ser. No. 08/000,000, entitled "Monoclonal Antibodies Specific for Advanced Glycosylation Endproducts in Biological Samples," filed Dec. 29, 1995) displayed recognition of disodium 6-(N-carboxymethylamino)caproate, designated in the Table as ALT-927. The results are given below in Table 1.

TABLE 1

MAb Characterization

| Antigen (conc. units) | Concentration of Antigen for 50% Inhibition of | | |
|---|---|---|---|
| | mAb BH4 | mAb 2G6 | mAb 4G9 |
| ALT-927 (pmol/well) | 5.7 | 21 | 11 |

Competitive ELISA: Plates coated with BSA-AGE at 10 μg/ml. Values are amount of inhibitor needed for 50% inhibition of binding. In the case of isothiocyanate the plates are soaked for 15 minutes with varying concentrations of isothiocyanate and the level of binding then measured.

Thus, these monoclonal antibodies, which independently recognize AGEs on different proteins, peptides and amino acids which arise from reaction with different reducing sugars have been shown to recognize 6-(N-carboxymethylamino)caproates, the compounds of this invention, and specifically, disodium 6-(N-carboxymethylamino)caproate. This allows the compounds of the present invention to be utilized as a pure substrate for the production of antibodies which will recognize these AGEs.

EXAMPLE 2

Production of a Monoclonal Antibody

A monoclonal antibody to the compounds of formula I reactive with in vivo-produced AGEs can be produced as follows.

Preparation of Immunogen: In accordance with the procedure described in Chang et al., *J. Biol. Chem.,* 260:7970–7974, 1985, one gram of disodium 6-(N-carboxymethylamino)caproate is coupled to a protein, KLH (Sigma Cat.#2133), and combined with 96 gm glucose in 500 ml of a 400 mM sodium phosphate buffer, pH 7.4. The solution was deoxygenated by bubbling nitrogen into the solution, and filter sterilized by passing the solution through a 0.2 micron cellulose acetate filter. After incubation at 37° C. for 90 days, the solution was dialyzed against a 20 mM sodium phosphate buffer, containing 0.15 M NaCl, pH 7.4. The protein content was determined using a Lowry assay, again filter sterilized, and aliquoted. The aliquots were stored at −80° C. until used.

Immunization Schedule: Five mice were pre-bled and earmarked. Each mouse was immunized subcutaneously with 0.2 ml of a preparation containing 100 μg of the Immunogen prepared above mixed 1:1 with Complete Freund's Adjuvant (CFA). Mice were boosted subcutaneously at day 21 with 0.2 ml of 50 μg of Immunogen in Incomplete Freund's Adjuvant (IFA). A second boost of 50 μg of Immunogen in IFA was administered on day 41 as before. Finally, a third boost of 50 μg of Immunogen in IFA was administered on day 63 as before and a test bleed taken from the tall vein and serum prepared. The mouse showing the highest titer as determined in the Antisera Test Bleed Titering procedure described below was selected and boosted intravenously with 0.1 ml containing 50 μg of Immunogen without adjuvant. Three days later, the spleen was removed and the animal exsanguinated.

Antisera Test Bleed Titering: An initial dilution of 1/100 of each serum sample to be titered was prepared in PBS containing 0.1% BSA, followed by 10 serial 2-fold dilutions in the same buffer for titer determination. Pre-immune sera noted above were diluted in the same manner as the immune sera and used as controls. Microtiter wells were coated with 1.5 μg of BSA-AGE antigen prepared by incubating bovine serum albumin (BSA) from Calbiochem, Catalog #12657, as described by Makita et al., *J. Biol. Chem.,* 267(8), pp. 5133–5138 (1992). The antigen coated wells were sealed with Mylar sealing tape (Corning) and incubated overnight at 4° C. The microtiter plates were subsequently washed 6 times with TBS-T Wash Solution and blocked for one hour at 37° C. by adding 200 ul of a solution of PBS containing 0.2% BSA and 0.2% sodium azide. The microtiter plates were washed as before and 100 μl of the dilutions of pre-immune and immune sera were added. After incubation for 2 hours at room temperature, the microtiter plates were washed as described above and 100 ul of a goat anti-mouse IgG (gamma chain specific) horseradish peroxidase-conjugated antibody (Sigma) was added to all wells and incubated for 1 hour at 37° C. The microtiter plates were washed as before and 100 ul of OPD Peroxidase Substrate (Sigma) was added to all wells and incubated for 30 minutes at room temperature. After the incubation period, the plates were read at 450 nm on a microtiter plate reader.

Hybridoma production was carried out by fusing the mouse spleen cells with the myeloma X63AG8.653 cell line as described elsewhere (Harlow, E. and D. Lane, Antibodies: A Laboratory Manual, Cold Spring Harbor Laboratory, 1988).

Hybridoma Screening Procedure: After fusion of spleen cells with the myeloma cell line, 1 drop of the 50 ml fusion mixture was added to each of 96 wells in 10 microwell cell culture plates (Corning). The plates were numbered 1 to 10, the rows of each plate by letter, and the columns by number to give a coding system that identified the parental cell cultures that developed from each drop of the fusion mixture. After culture in selection media described in Harlow and Lane, supra, hybridoma cultures were screened for antibody production to the antigen as follows:

Immunogen coated wells were prepared as described in the Antisera Test Bleed Titering section above. Further, BSA was coated on wells following the same coating procedure as with Immunogen to detect any nonspecific binding. The antigen coated plates were used to screen cell culture supernates from each of the parental cultures. The parental supernates were diluted 1:2 in PBS containing 0.2% BSA and 100 μl of each added to one well of an Immunogen coated microtiter plate and to one well of a BSA coated plate. The plates were incubated at room temperature for 2 hours and subsequently washed 6 times with TBS-T Wash Solution. One hundred μl of a goat anti-mouse IgG (gamma chain specific) horseradish peroxidase-conjugated antibody diluted 1:1000 in PBS containing 1% BSA was added to each well and the procedure followed as in the Antisera Test Bleed Titering section above. Sixteen parental cultures were found to produce absorbance readings exceeding 0.3 O.D. on the BSA-AGE wells and no reactivity on the BSA coated wells. The latter parental cultures were expanded in culture in 24 well macrowell plates (Corning) and upon further supernatant/antibody evaluation, three parental cultures were re-cloned (secondary cloning). Following a procedure described in Harlow and Lane, supra, the parental cultures were diluted in RPMI 1640 culture medium containing 20% fetal bovine serum to give a cell density of 0.5–10 cells per well on wells that were precultured with splenocyte feeder cells.

After two weeks, parental cell cultures yielding Immunogen-specific producing antibody clones were identified by testing the culture supernates in the screening procedure above. After expansion of these clones in cell culture, one clonal culture was selected that had high viability and produced the highest titer antibody to Immunogen in the aforementioned antibody screening assay. A further subcloning of the latter was done to assure monoclonality. A tertiary cloning was done as above, and subclones were identified that produced good titers to Immunogen from the 0.3 cells/well dilution. One was selected from this group based on a comparative affinity analysis in accordance with Macdonald et al. (Macdonald et al., 1988, *Journal of Immunological Methods,* 106:191–194). The cells from each culture were prepared in accordance with Harlow and Lane, supra for frozen storage, and expanded in culture and adapted to a protein-free medium (MaxiCell/Hybridoma-PF Medium, Cat. No. N10105, Atlanta Biologicals, Norcross, Ga.) for monoclonal antibody production.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of raising an antibody to an advanced glycosylation endproduct which comprises using as the immunogen, a 6-(N-carboxymethylamino)caproate of the formula $$XO_2C-(CH_2)_5-NH-CH_2CO_2X \qquad (I)$$

wherein X is hydrogen or an alkali metal salt cation.

2. The method of claim 1 wherein the compound of formula I is disodium 6-(N-carboxymethylamino)caproate.

3. A method of determining the purity of a monoclonal antibody to an advanced glycosylation endproduct which comprises determining the reactivity of the monoclonal antibody under test to a composition comprising a 6-(N-carboxymethylamino)caproate of the formula $$XO_2C-(CH_2)_5-NH-CH_2CO2X \qquad (I)$$

wherein X is hydrogen or an alkali metal salt cation.

4. The method of claim 3 which comprises using disodium 6-(N-carboxymethylamino)caproate.

* * * * *